United States Patent
Uber, III

(10) Patent No.: US 7,427,281 B2
(45) Date of Patent: Sep. 23, 2008

(54) METHOD OF DELIVERING FLUID MIXTURES TO MULTIPLE PATIENTS

(75) Inventor: Arthur E. Uber, III, Pittsburgh, PA (US)

(73) Assignee: Medrad, Inc., Indianola, PA (US)

(*) Notice: Subject to any disclaimer, the term of this patent is extended or adjusted under 35 U.S.C. 154(b) by 346 days.

(21) Appl. No.: 09/939,656

(22) Filed: Aug. 28, 2001

(65) Prior Publication Data

US 2002/0026148 A1  Feb. 28, 2002

Related U.S. Application Data

(60) Division of application No. 09/575,809, filed on May 22, 2000, now Pat. No. 6,306,117, which is a continuation of application No. 09/102,554, filed on Jun. 23, 1998, now Pat. No. 6,149,627, which is a continuation of application No. 08/755,755, filed on Oct. 21, 1996, now Pat. No. 5,843,037, which is a continuation of application No. 08/144,460, filed on Oct. 28, 1993, now abandoned.

(51) Int. Cl.
*A61M 31/00* (2006.01)
(52) U.S. Cl. ...................................................... 604/508
(58) Field of Classification Search ............ 604/65–67, 604/151, 82, 131, 246, 533–539, 284, 171, 604/500, 508; 128/DIG. 12, DIG. 13, DIG. 1; 600/431, 432
See application file for complete search history.

(56) References Cited

U.S. PATENT DOCUMENTS

| | | | |
|---|---|---|---|
| 3,349,713 A | 10/1967 | Fassbender | |
| 3,523,523 A | 8/1970 | Reich | |
| 3,623,474 A | 11/1971 | Heilman et al. | |
| 3,701,345 A | 10/1972 | Heilman | |
| 3,755,655 A | 8/1973 | Sewecal | |
| 3,793,600 A | 2/1974 | Groubard | |
| 3,812,843 A | 5/1974 | Wjutten | |
| 3,888,239 A | 6/1975 | Rubenstein | |
| 3,895,220 A | 7/1975 | Nelson | |
| 3,898,983 A | 8/1975 | Elam | |
| 3,927,955 A | 12/1975 | Spinosa | |
| 3,941,126 A | 3/1976 | Dietrich | |
| 3,958,103 A | 5/1976 | Oka | |
| 3,968,195 A | 7/1976 | Bishop | |
| 3,995,381 A | 12/1976 | Manfred | |

(Continued)

FOREIGN PATENT DOCUMENTS

CA  2045070  2/1992

(Continued)

OTHER PUBLICATIONS

"Disposable Low-Cost Catheter Tip Sensor Measures Blood Pressure During Surgery", Sensor, Jul. 1989.

*Primary Examiner*—Matthew F Desanto
(74) *Attorney, Agent, or Firm*—Gregory Bradley; Jeffrey Karceski

(57) ABSTRACT

An injection apparatus for delivering fluid to multiple patients includes a first fluid source, a second fluid source, and a fluid path disposed between the first and second fluid sources and a patient. The fluid path includes a mixing device, a reusable portion for delivering fluid to multiple patients and a per-patient disposable portion removably connected to the reusable portion.

20 Claims, 6 Drawing Sheets

U.S. PATENT DOCUMENTS

| | | |
|---|---|---|
| 4,001,549 A | 1/1977 | Corwin |
| 4,038,981 A | 8/1977 | LeFevre |
| 4,090,502 A | 5/1978 | Tajika |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,207,871 A | 6/1980 | Jenkins |
| 4,223,675 A | 9/1980 | Williams |
| 4,262,824 A | 4/1981 | Hrynewycz |
| 4,280,494 A | 7/1981 | Cosgrove |
| 4,284,073 A | 8/1981 | Krause |
| 4,319,568 A | 3/1982 | Tregouing |
| 4,340,153 A | 7/1982 | Spivey |
| 4,341,153 A | 7/1982 | Bowser |
| 4,392,849 A | 7/1983 | Petre |
| 4,396,385 A | 8/1983 | Kelly |
| 4,402,310 A | 9/1983 | Kimura |
| 4,409,966 A | 10/1983 | Lambrecht et al. |
| 4,434,822 A | 3/1984 | Bellamy |
| 4,444,198 A | 4/1984 | Petre |
| 4,447,230 A | 5/1984 | Gula |
| 4,479,760 A | 10/1984 | Bilstad |
| 4,479,761 A | 10/1984 | Bilstad |
| 4,479,762 A | 10/1984 | Bilstad |
| 4,512,764 A | 4/1985 | Wunsch |
| 4,544,949 A | 10/1985 | Kurihara |
| 4,551,133 A | 11/1985 | Zegers de Beyl |
| 4,559,036 A | 12/1985 | Wunsch |
| 4,563,175 A | 1/1986 | LaFond |
| 4,585,009 A | 4/1986 | Barker |
| 4,585,941 A | 4/1986 | Bergner |
| 4,610,670 A | 9/1986 | Spencer |
| 4,610,790 A | 9/1986 | Reti |
| 4,633,307 A | 12/1986 | Honda |
| 4,634,426 A | 1/1987 | Kamen |
| 4,636,144 A | 1/1987 | Abe |
| 4,655,197 A | 4/1987 | Atkinson |
| 4,662,906 A | 5/1987 | Matkovich |
| 4,682,170 A | 7/1987 | Kubata |
| 4,710,166 A * | 12/1987 | Thompson et al. ............ 604/81 |
| 4,750,643 A * | 6/1988 | Wortrich ..................... 604/173 |
| 4,754,786 A * | 7/1988 | Roberts ..................... 222/482 |
| 4,756,706 A * | 7/1988 | Kerns et al. ................... 604/66 |
| 4,781,687 A | 11/1988 | Wall |
| 4,783,273 A | 11/1988 | Knutsson |
| 4,798,590 A | 1/1989 | O'Leary |
| 4,823,833 A | 4/1989 | Hogan |
| 4,835,521 A | 5/1989 | Andrejasich |
| 4,836,187 A | 6/1989 | Iwakoshi et al. |
| 4,838,856 A | 6/1989 | Mulreany et al. |
| 4,840,620 A | 6/1989 | Kobayashi |
| 4,844,052 A | 7/1989 | Iwakoshi et al. |
| 4,853,521 A | 8/1989 | Claeys |
| 4,854,301 A | 8/1989 | Nakajima |
| 4,854,324 A | 8/1989 | Hirschman |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz |
| 4,887,208 A | 12/1989 | Schneider |
| 4,887,554 A | 12/1989 | Whitford |
| 4,925,444 A * | 5/1990 | Orkin et al. ................... 604/80 |
| 4,929,818 A | 5/1990 | Bradbury |
| 4,935,005 A | 6/1990 | Haines |
| 4,936,832 A | 6/1990 | Vaillancourt |
| 4,943,279 A | 7/1990 | Samiotes |
| 4,946,439 A | 8/1990 | Eggers |
| 4,950,245 A | 8/1990 | Brown |
| 4,954,129 A | 9/1990 | Giuliani et al. |
| 4,976,687 A | 12/1990 | Martin |
| 4,978,335 A | 12/1990 | Arthur |
| 4,981,467 A | 1/1991 | Bobo |
| 5,004,472 A | 4/1991 | Wallace |
| 5,009,654 A | 4/1991 | Minshall |
| 5,032,112 A | 7/1991 | Fairchild |
| 5,053,002 A | 10/1991 | Barlow |
| 5,059,173 A | 10/1991 | Sacco |
| 5,061,243 A | 10/1991 | Winchell et al. |
| 5,078,683 A | 1/1992 | Sancoff |
| 5,088,981 A | 2/1992 | Howson |
| 5,100,380 A | 3/1992 | Epstein |
| 5,104,374 A | 4/1992 | Bisko et al. |
| 5,104,387 A | 4/1992 | Pokorney et al. |
| 5,108,365 A | 4/1992 | Woods, Jr. |
| 5,113,904 A | 5/1992 | Aslanian |
| 5,128,121 A | 7/1992 | Berg |
| 5,133,336 A | 7/1992 | Savitt et al. |
| 5,135,000 A | 8/1992 | Kami et al. |
| 5,163,909 A * | 11/1992 | Stewart ....................... 604/140 |
| 5,180,896 A | 1/1993 | Gibby |
| 5,191,878 A | 3/1993 | Iida et al. |
| 5,196,007 A | 3/1993 | Ellman et al. |
| 5,199,604 A | 4/1993 | Palmer |
| 5,207,642 A * | 5/1993 | Orkin et al. .................... 604/65 |
| 5,230,614 A | 7/1993 | Zanger |
| 5,242,390 A | 9/1993 | Goldrath |
| 5,267,174 A | 11/1993 | Kaufman |
| 5,269,756 A | 12/1993 | Dryden |
| 5,273,537 A | 12/1993 | Haskvitz |
| 5,274,218 A | 12/1993 | Vata |
| 5,310,997 A | 5/1994 | Roach |
| 5,313,992 A | 5/1994 | Grabenkort |
| 5,317,506 A | 5/1994 | Coutre |
| 5,328,463 A | 7/1994 | Barton |
| 5,329,459 A | 7/1994 | Kaufman |
| 5,339,799 A | 8/1994 | Kami |
| 5,349,625 A | 9/1994 | Born |
| 5,354,273 A | 10/1994 | Hagen |
| 5,361,761 A | 11/1994 | Van Lysel |
| 5,362,948 A | 11/1994 | Mormoto |
| 5,368,562 A | 11/1994 | Blomquist |
| 5,376,070 A | 12/1994 | Purvis et al. |
| 5,378,231 A | 1/1995 | Johnson |
| 5,382,232 A | 1/1995 | Hauge et al. |
| 5,385,540 A | 1/1995 | Abbott |
| 5,417,213 A | 5/1995 | Prince |
| 5,431,627 A | 7/1995 | Pastrone |
| 4,946,256 A | 8/1995 | Kumble |
| 5,445,621 A | 8/1995 | Poli |
| 5,450,847 A * | 9/1995 | Kampfe et al. .............. 600/420 |
| 5,458,128 A | 10/1995 | Polanyi |
| 5,460,609 A | 10/1995 | O'Donnell |
| 5,464,391 A | 11/1995 | DeVale |
| 5,468,240 A | 11/1995 | Genetelia et al. |
| 5,472,403 A | 12/1995 | Comacchia et al. |
| 5,474,683 A | 12/1995 | Bryant |
| 5,485,831 A | 1/1996 | Holdsworth |
| 5,489,265 A | 2/1996 | Montalvo |
| 5,494,036 A | 2/1996 | Uber, III |
| 5,494,822 A | 2/1996 | Sadri |
| 5,496,273 A | 3/1996 | Pastrone |
| 5,507,412 A | 4/1996 | Ebert |
| 5,515,851 A | 5/1996 | Goldstein |
| 5,522,798 A | 6/1996 | Johnson |
| 5,531,679 A | 7/1996 | Schulman |
| 5,531,697 A | 7/1996 | Olsen |
| 5,533,978 A | 7/1996 | Teirstein |
| 5,547,470 A | 8/1996 | Johnson |
| 5,552,130 A | 9/1996 | Kraus |
| 5,553,619 A | 9/1996 | Prince |
| 5,560,317 A | 10/1996 | Bunyan et al. |
| 5,569,208 A | 10/1996 | Woelpper |
| 5,573,515 A | 11/1996 | Wilson |

| | | | | | |
|---|---|---|---|---|---|
| 5,579,767 A | 12/1996 | Prince | 2004/0015078 A1 | 1/2004 | Evans, III et al. |

FOREIGN PATENT DOCUMENTS

| | | |
|---|---|---|
| 5,590,654 A | 1/1997 | Prince |
| 5,592,940 A | 1/1997 | Kampfe et al. |
| 5,616,124 A | 4/1997 | Hague |
| 5,768,405 A | 6/1998 | Markam-Ebeid |
| 5,799,649 A | 9/1998 | Prince |
| 5,800,397 A | 9/1998 | Wilson |
| 5,806,519 A * | 9/1998 | Evans et al. ............... 600/431 |
| 5,840,026 A | 11/1998 | Uber, III et al. |
| 5,843,037 A | 12/1998 | Uber, III |
| 5,882,343 A | 3/1999 | Wilson |
| 5,885,216 A | 3/1999 | Evans, III et al. |
| 5,916,165 A | 6/1999 | Duchon |
| 5,988,587 A | 11/1999 | Duchon |
| 6,099,502 A | 8/2000 | Duchon |
| 6,149,627 A | 11/2000 | Uber, III |
| 6,221,045 B1 | 4/2001 | Duchon et al. |
| 6,306,117 B1 | 10/2001 | Uber, III |
| 6,344,030 B1 | 2/2002 | Duchon et al. |
| 6,385,483 B1 | 5/2002 | Uber et al. |
| 6,442,418 B1 | 8/2002 | Evans, III et al. |
| 6,626,862 B1 | 9/2003 | Duchon et al. |
| 6,656,157 B1 | 12/2003 | Duchon et al. |
| 2003/0050556 A1 | 3/2003 | Uber, III et al. |

| | | |
|---|---|---|
| DE | 3726452 | 1/1989 |
| DE | 41 21 568 | 10/1992 |
| DE | 41 21 568 A1 | 10/1992 |
| DE | 44 26 387 | 8/1995 |
| EP | 0 189 491 | 8/1986 |
| EP | 0 337 924 | 10/1989 |
| EP | 0343501 | 11/1989 |
| EP | 0 600 448 | 6/1994 |
| EP | 0 619 122 | 10/1994 |
| EP | 0 650 738 | 5/1995 |
| EP | 0 650 739 | 5/1995 |
| EP | 0 702 966 | 3/1996 |
| FR | 2492708 | 5/1982 |
| FR | 2561949 | 10/1985 |
| GB | 2 207 749 | 2/1989 |
| GB | 2252656 | 8/1992 |
| WO | WO 80/01754 | 9/1980 |
| WO | WO 85/00292 | 1/1985 |
| WO | WO 88/03815 | 6/1988 |
| WO | WO 94/15664 | 7/1994 |
| WO | WO 96/32975 | 10/1996 |
| WO | WO 99/24095 | 5/1999 |

* cited by examiner

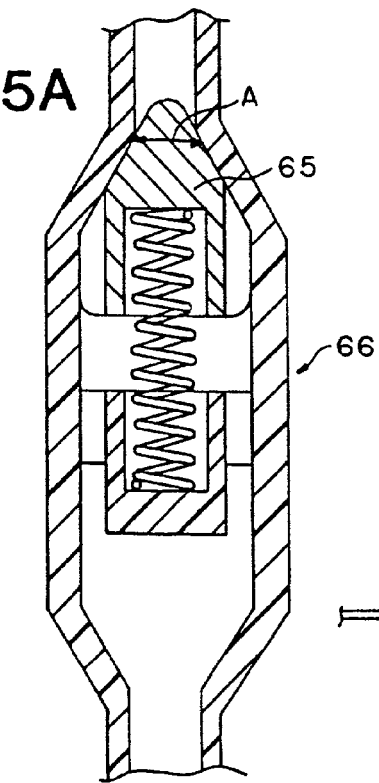
FIG. 5A
FIG. 5B
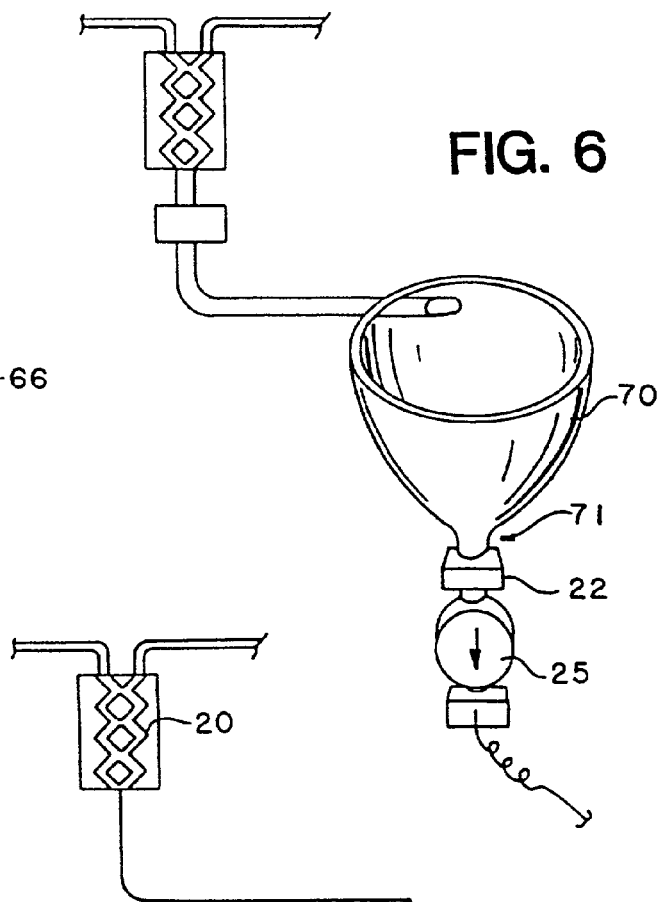
FIG. 6
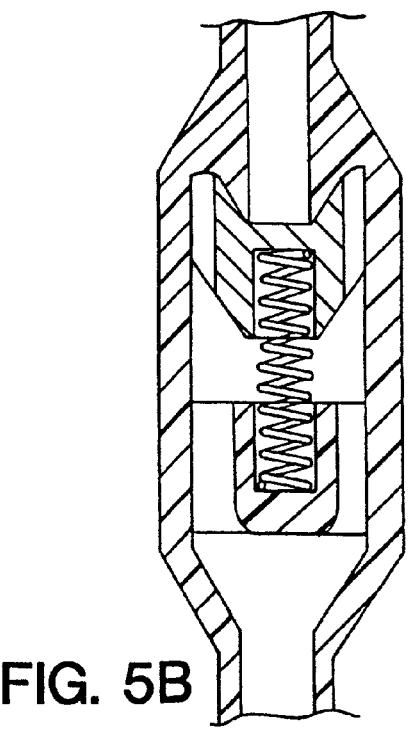
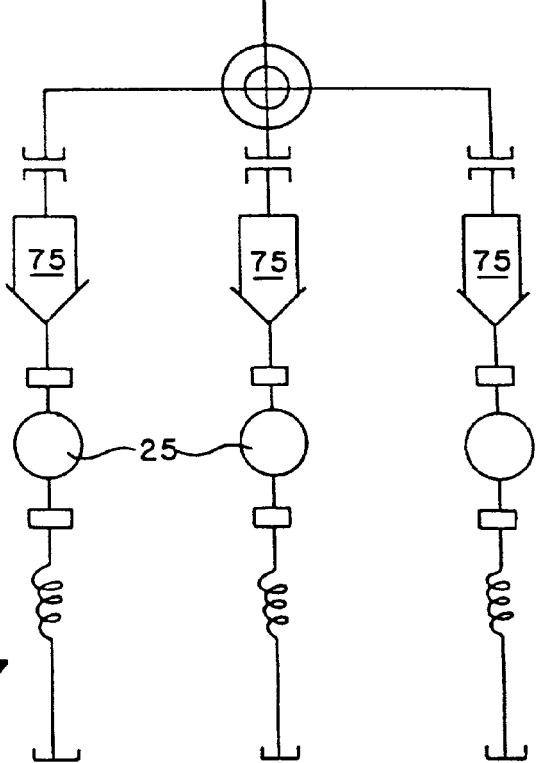
FIG. 7

METHOD OF DELIVERING FLUID MIXTURES TO MULTIPLE PATIENTS

This application is a continuation of U.S. application Ser. No. 09/575,809 (U.S. Pat. No. 6,306,117) filed May. 22, 2000, which is a continuation of U.S. application Ser. No. 09/102,554 (U.S. Pat. No. 6,149,627) filed Jun. 23, 1998, which is a continuation of U.S. application Ser. No. 08/755,755 (U.S. Pat. No. 5,843,037) filed Oct. 21, 1996, which is a continuation of U.S. application Ser. No. 08/144,460 (abandoned) filed Oct. 28, 1993, each of which is hereby incorporated by reference in its entirety.

BACKGROUND OF THE INVENTION

In U.S. Pat. No. 5,569,181 assigned to the same Assignee as the present invention, discussion was undertaken with regard to the problems arising from the potential cross-contamination that can occur with a multi-patent fluid dispensing system. One facet of the system provided involves prevention of contamination of the multi-use segment of the fluid path during the time the system is connected to the patient. The disclosed system utilized one of the two methods: a back flow preventing valve and a sterile filter, or a physical separation achieved by filling a dose container and separating the dose container from the filling fluid path before connection to the patient.

A back flow valve and a sterile filter combination should give sufficient protection. Bacteria cannot penetrate the filter. Viruses and proteins can penetrate the filter but are not active, and so cannot swim upstream. They can only diffuse. The drawbacks to this approach involve the pressure drop through the filter and volume of fluid remaining in the filter. Also, there is no way to verify that the filter is not leaking.

The present invention deals with additional methods of preventing contamination of the reusable fluid path by the patient being injected. To achieve the improved methods of preventing contamination, the present invention embodies the concept of preventing back flow, by providing no open fluid path through which bacteria can migrate or viruses or pyrogens can diffuse. (If a path is open, the velocity can then be made sufficient to prevent back diffusion.) Additionally, turbulence must be avoided since turbulence necessarily involves reverse flows and eddys that can carry material against the flow, unless the flow is high enough to prevent any part of the fluid from having a net upstream velocity vector.

Means of preventing contamination of the fluid path by contaminants other than the patient being injected are presented in U.S. Pat. No. 5,806,519. Any of the concepts presented there may be matched with any of the embodiments presented here. The relevant feature is the "per patient" connection.

OBJECTS OF THE INVENTION

It is a principal object of this invention to provide an improved apparatus for injecting a fluid medium into a plurality of patients while minimizing the chance of cross-contamination.

It is another object of this invention to provide an apparatus for injecting fluid mediums into patients in which there is no continuous stream of fluid existing between the source of the fluid and the patient.

It is another object of this invention to provide an apparatus in which a peristaltic apparatus is present which precludes the reverse flow of substances from the patient towards the origin of the fluid to be injected.

Other objects and advantages of this invention will be in part obvious and in part explained by reference to the accompanying specification and drawings in which:

DESCRIPTION OF THE DRAWINGS

FIGS. 5a and 5b are diagrammatic illustrations of an apparatus in which there is a biased element to preclude reverse flow of fluid from the patient towards the source of medical fluid;

FIG. 6 is a diagrammatic view showing one form of an apparatus for creating a discontinuous flow of medical fluid;

FIG. 7 is a diagrammatic showing of another type of apparatus having discontinuous flow and a plurality of patient connections;

DESCRIPTION OF THE INVENTION

Figure 1:
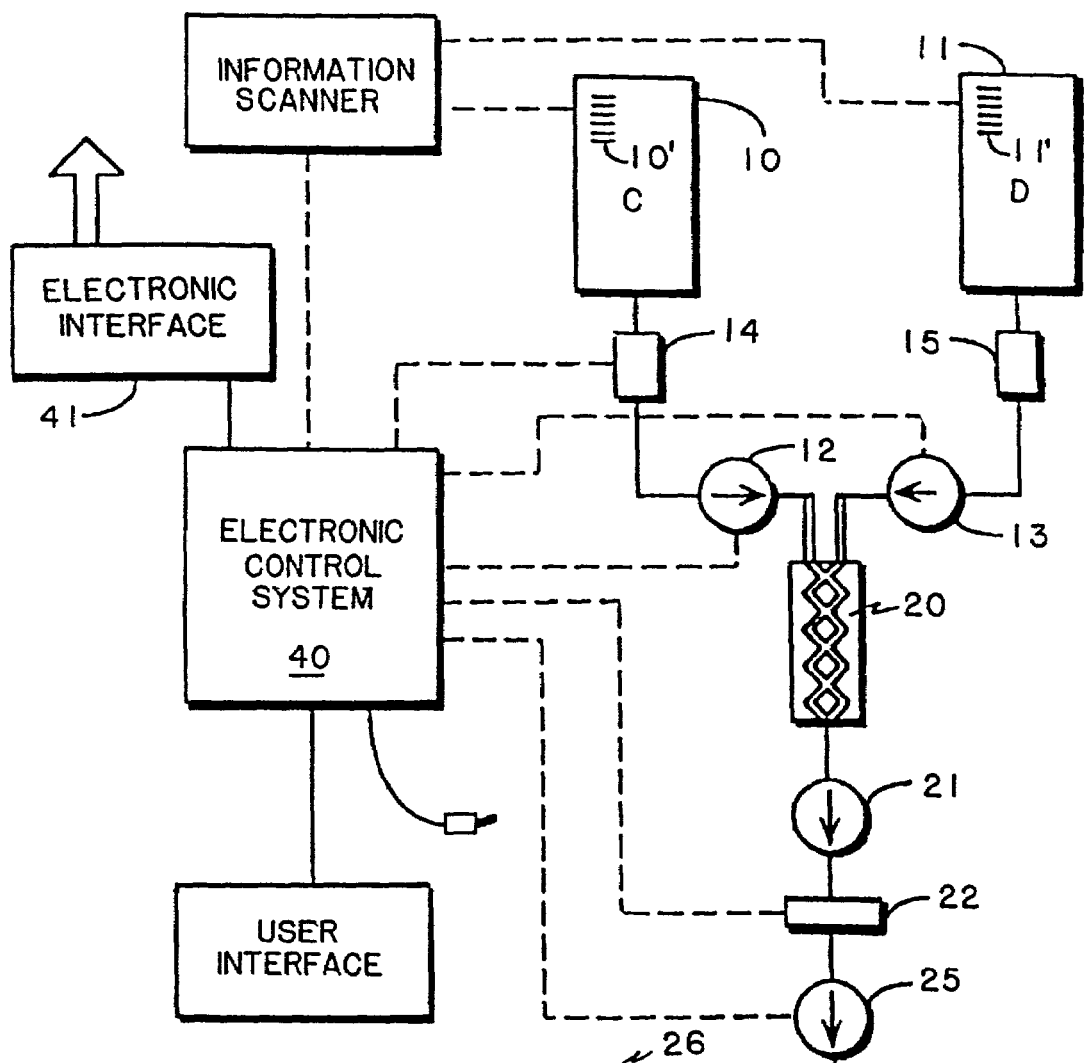
FIG. 1 diagrammatically shows an apparatus and a system for injecting a fluid medium directly into a patient which minimizes the chance of patient-to-patient cross-contamination.
Figure 1:
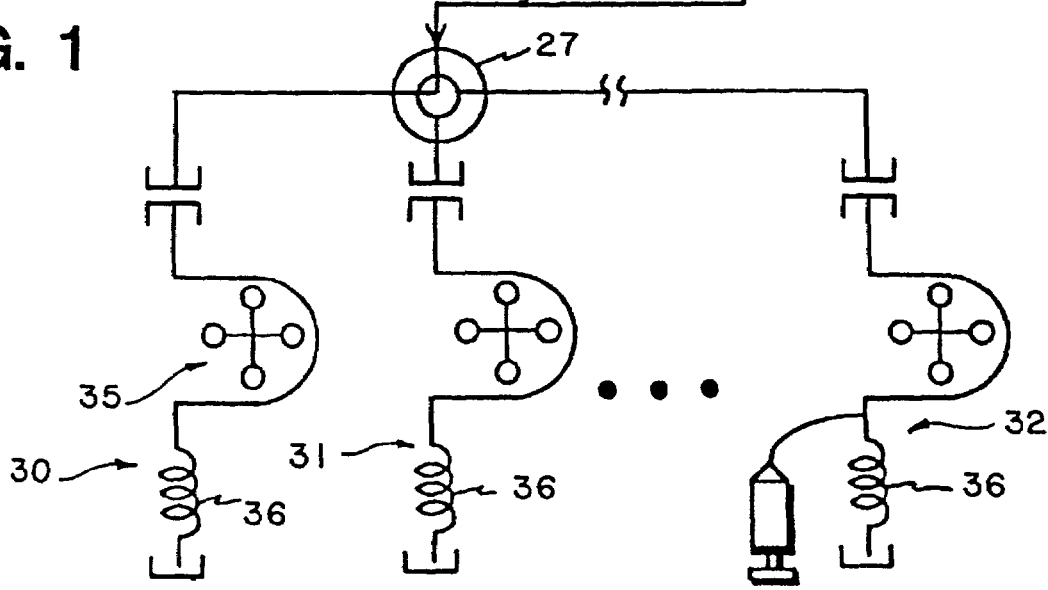

To better understand the present invention, reference is made to the drawings, and specifically to FIG. 1 there is provided a source of fluid medium which is contained within a bulk container 10. Numeral 11 represents a similar container that is used to hold a supply of diluent, in the event that it is desired to reduce the concentration of the fluid medium contained within source 10. A metering pump 12 draws fluid from the supply source 10 at the proper flow rate. The second metering pump 13 draws diluent (when desired) from the bulk reservoir 11 within which the supply of diluent is contained. A preferred metering pump is a precision peristaltic pump with santoprene tubing. A pump wall design similar to that of U.S. Pat. No. 5,236,014 would minimize the pulsatile flow characteristics. As the fluids are removed from containers 10 and 11, they are heated by means of heaters 14 and 15 so that they approximate body temperature. The heating, of course, can decrease the viscosity and make the fluid more comfortable for the patient. Upon leaving the metering pumps 12 and 13, the fluids meet as they are joined and flow through a static mixer 20 that contains helical vanes. The company ConProTech makes many sizes and lengths, some with polypropylene vanes and case. These static mixers are designed for mixing fluids with very different viscosities and varying dilution ratios. The exact length and diameter to be used will depend to some degree upon the viscosity of the substances being co-mingled. The mixture then flows through a fluid assurance device 22 which many be an ultrasonic detector so that the presence or absence of air in the fluid can be determined. Since these types of devices cannot detect small air bubbles, by being located before a pressurization pump 25, bubbles will be as large as possible. It helps minimize the chance that a broken line or human error can inject air into the patient. From pressurizing pump 25, a supply conduit 26 leads to a rotary switch 27 that can distribute fluid between the individual or "per patient" hookups 30, 31 and 32. Each of the individual connections contains what has been diagrammatically shown as a section to mate with a peristaltic apparatus 35. Each per patient disposable tube 36 is placed in a peristaltic apparatus 35 before being connected to the patient. Then it is connected to the patient and the injection is completed. The disposable connector tube 36 is disconnected from the patient. The rotary valve is turned to seal off the opening and the tube removed from the peristaltic apparatus and the connection to the rotary valve. This portion is then discarded. The next tube should be placed in the peristaltic apparatus.

This is a good strategy but it requires operator vigilance to make sure that the line is in the peristaltic device before being connected to the patient and that the rotary valve is moved before the line is removed from the peristaltic device. Interlocks and intermediate all/off positions on the rotary switch could be provided. The rotary valve could have a "no connection" position between each connection position. The interlocks could function such that the rotary valve cannot be moved to access an output line until the line is in the peristaltic device, and another interlock could require that the rotary valve be turned to the intermediate off before the tubing can be removed from the peristaltic pump.

The present apparatus includes an electronic control system (ECS) 40 to assure that the needs of the patient are met safely. ECS 40 gets information on the contents of the bulk reservoirs 10 and 11. The preferred method is to read bar codes indicated by numerals 10' and 11' respectively. Another way is to quiz the operator to enter the data each time a bulk reservoir is changed, and then store that information. The operator would read the label on or packaged with the bulk reservoir, and enter the appropriate data. This need only be done when a bulk reservoir is changed.

With each injection, the operator needs to tell the system what to do. The data most similar to present practice is: 1) the concentration desired, 2) the flow rate, and 3) the total volume to be delivered. Present practice also includes multiple phases with various flow rates during each phase. This system would allow various contrast concentrations during each flow rate as well.

However, given the capabilities of this system, a preferred set of information is: 1) the procedure being done, and 2) the patient weight. This way the contrast dose could be optimized for the patient. The algorithm would have been previously provided information on milligrams of iodine per kilogram of patient for each procedure when the system was first installed in the hospital. It could display concentration, flow rate and volume for operator verification, if the operator desired. An electronic interface 41 is shown which can connect to the hospital information system to get information on the patient, such as weight. Then the operator would only have to input the patient number. The electronic interface could also be connected to the imaging equipment. It could send or receive information so that, for instance, the operator only need to program the CT scanner with number of slices and body section, and this would be transmitted to the contrast delivery system to be used in determining flow rates and delays. The electronic interface would also be used to let the scanner trigger the contrast delivery system or vice versa, after the appropriate delays. A hard copy printer may be optionally part of the user interface, receiving data from the ECS. This can print a record of the actual injection for insertion into the patient records. The output may be alphanumeric or be a graphical representation of the injection.

The operation of delivering fluid to the patient can be started by the operator with a start switch on the contrast delivery system, or from the console of the scanner. There would need to be an arming procedure similar to that of present injectors to help assure patient safety.

In CT, usually only one injection is given, sometimes with pauses and changes in flow rates. As the end of the injection is reached, contrast can be conserved if the contrast flow is stopped and the diluent flow continued so the "bolus" of diluted contrast is flushed out of the tubing and into the patient. In angiography, several injections may be used. It is necessary to flush only after the last injection, although no harm, except injecting a little extra fluid, occurs if the flush follows each injection.

Another form of waste is using contrast to prime the fluid path which is disposed of with each patient, especially if the concentration has not yet been decided upon. The flush or diluent fluid is much cheaper than the contrast and of lower viscosity, so it can be used to prime the line and make sure that all air has been removed from the path to the patient.

Figure 2:
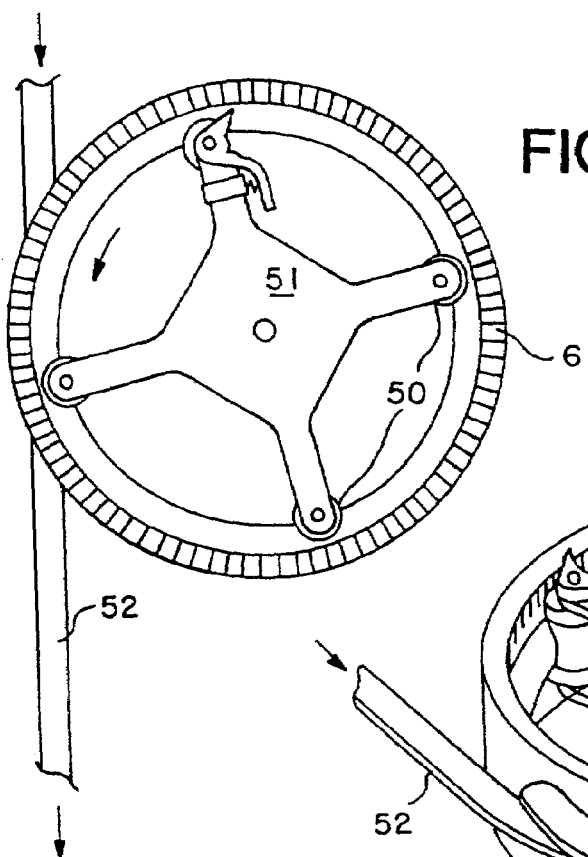
FIG. 2 is a form of peristaltic control apparatus that can be used in the cross-contamination preventing system of FIG. 1.
Figure 3:
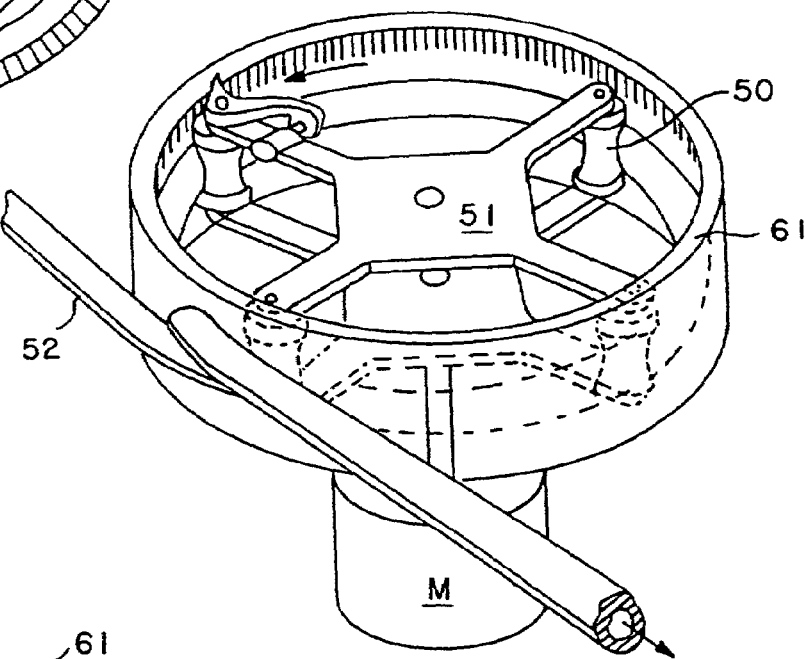
FIG. 3 is a front perspective of the apparatus of FIG. 2.
Figure 4:
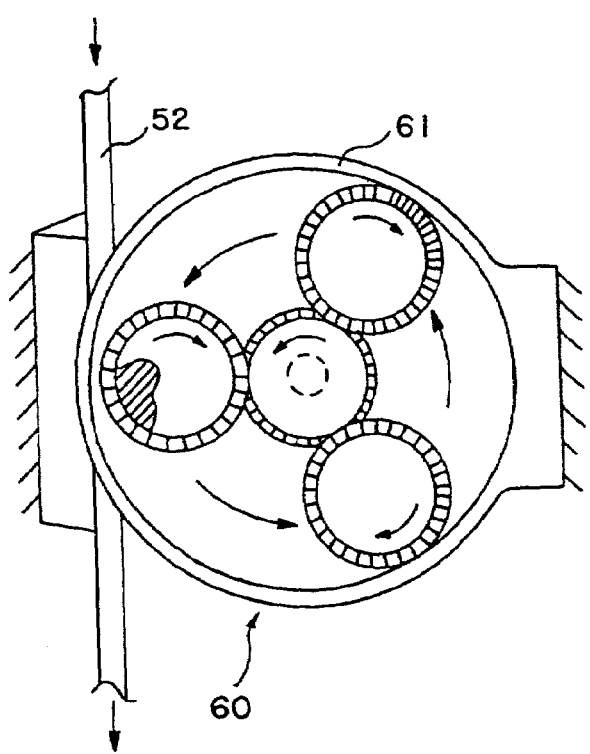
FIG. 4 is another diagram showing another type of peristaltic apparatus for use in the present invention.

Referring to FIGS. 2 and 3 an alternative would be to make the peristaltic mechanism be fixed with the tubing, rather than separate as shown in FIG. 1. It would be disposable, but, it could be a very simple disposable with four wheels on a cross and a band which held the tubing for one or more turns. (It could be less than one turn, but one or more is preferred to equalize the lateral forces.) This type of construction is shown in FIGS. 4 and 3 with numeral 50 indicating the wheels mounted on cross 51 and in contact with supply tubing 52. FIG. 4 shows an even simpler arrangement where the wheels form a planetary gear set 60, with the inner gear free to rotate. In this embodiment, it might be easier to have the ratchet mechanism on the band as shown at 61 in FIG. 3. This whole assembly does not need to be more than 1" across. While the peristaltic pump never has an open fluid path, turbulence can move material from the wall to the wall farther upstream. Thus, it is desirable, but not essential, that the tubing diameter be chosen to preserve laminar flow. Since the flow ranges differ by modality, the Reynolds number calculation, familiar to fluid mechanics, will need to be used to make this determination.

The peristaltic mechanism could be used as a flow sensor. It could be coupled to a shaft on the durable equipment or an optical sensor could detect when the gears pass. Another use of the peristaltic flow sensor is as a mechanical stop. Peristaltic flow sensor could be placed on the durable equipment in such a way that the ECS 40 read the number of revolutions and stop its rotation when the appropriate volume was reached. Because the peristaltic flow sensor has some friction, it also prevents flow through caused by gravity when the system is off. The integral disposable peristaltic mechanism would limit dripping when the "per patient" disposable is removed. This "per patient" disposable peristaltic pump would also be a convenient pumping means for other low pressure IV fluid injections.

In all the peristaltic mechanisms above, any type of peristaltic motion is acceptable. A linear peristaltic mechanism would work. Two lines may be run in parallel through out of phase peristaltic mechanisms and their outputs combined to significantly decrease pulsations.

Also, it is important to note that a peristaltic mechanism while effective is not sufficient to prevent cross-contamination, if turned backwards, either by operator action or by back pressure, for example. There should be back flow prevention means in the line, or preferably in the peristaltic mechanism itself.

Figure 8:
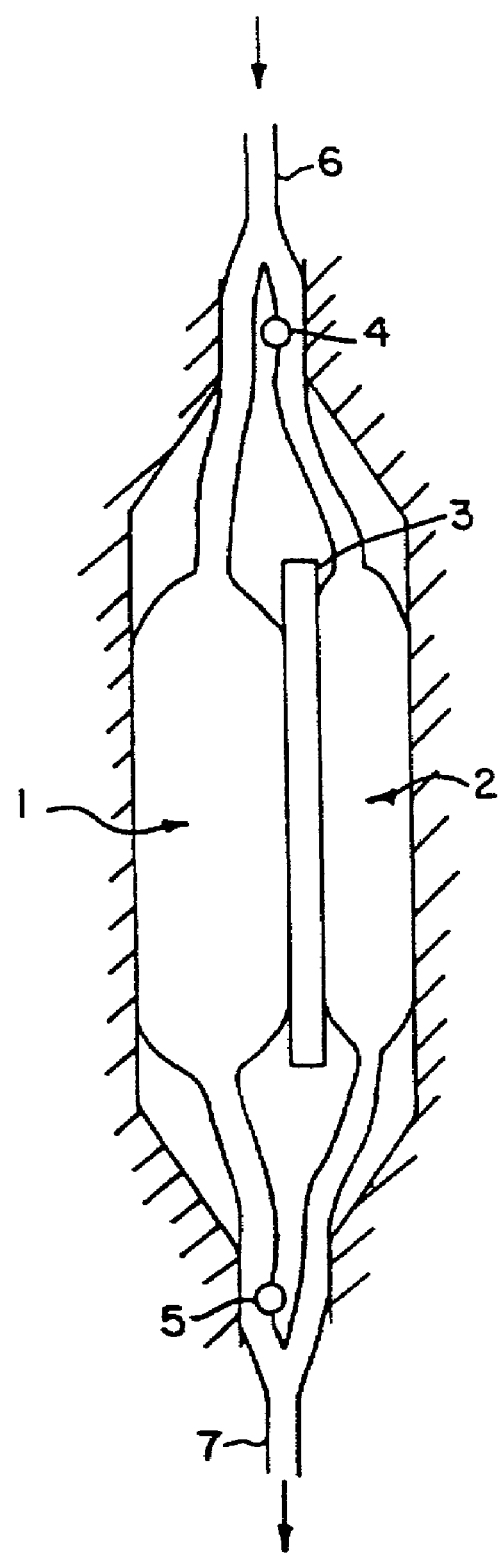
FIG. 8 is a diagrammatic showing of a packeted flow means.

FIG. 8 shows another means of dividing the fluid flow into discrete packets to prevent cross-contamination. This is a variation on the peristaltic idea, where the fluid path splits into two parts. In this figure, fluid is flowing into inlet 6 of chamber 1, its outlet 7 is blocked so the chamber expands and drives the pressure plate 3 against chamber 2. This drives fluid out of chamber 2 and on to the patient. When the pressure plate reaches the maximum designed travel, the inlet valve 4 and outlet valve 5 switch position, allowing chamber 2 to fill and chamber 1 to empty. This allows continuous fluid flow but never permits a continuously open fluid path to exist. It is preferred that the pressure plate upon reaching its end of travel mechanically trigger the inlet valves, and that there be a mechanical linkage between the valves so that they can not both simultaneously open to the same chamber. These controlling strategies could also be performed by the ECS, with redundancy and verification of valve positions. It is possible to extend this concept to using three or ore chambers, to get a more even flow.

Figure 10:
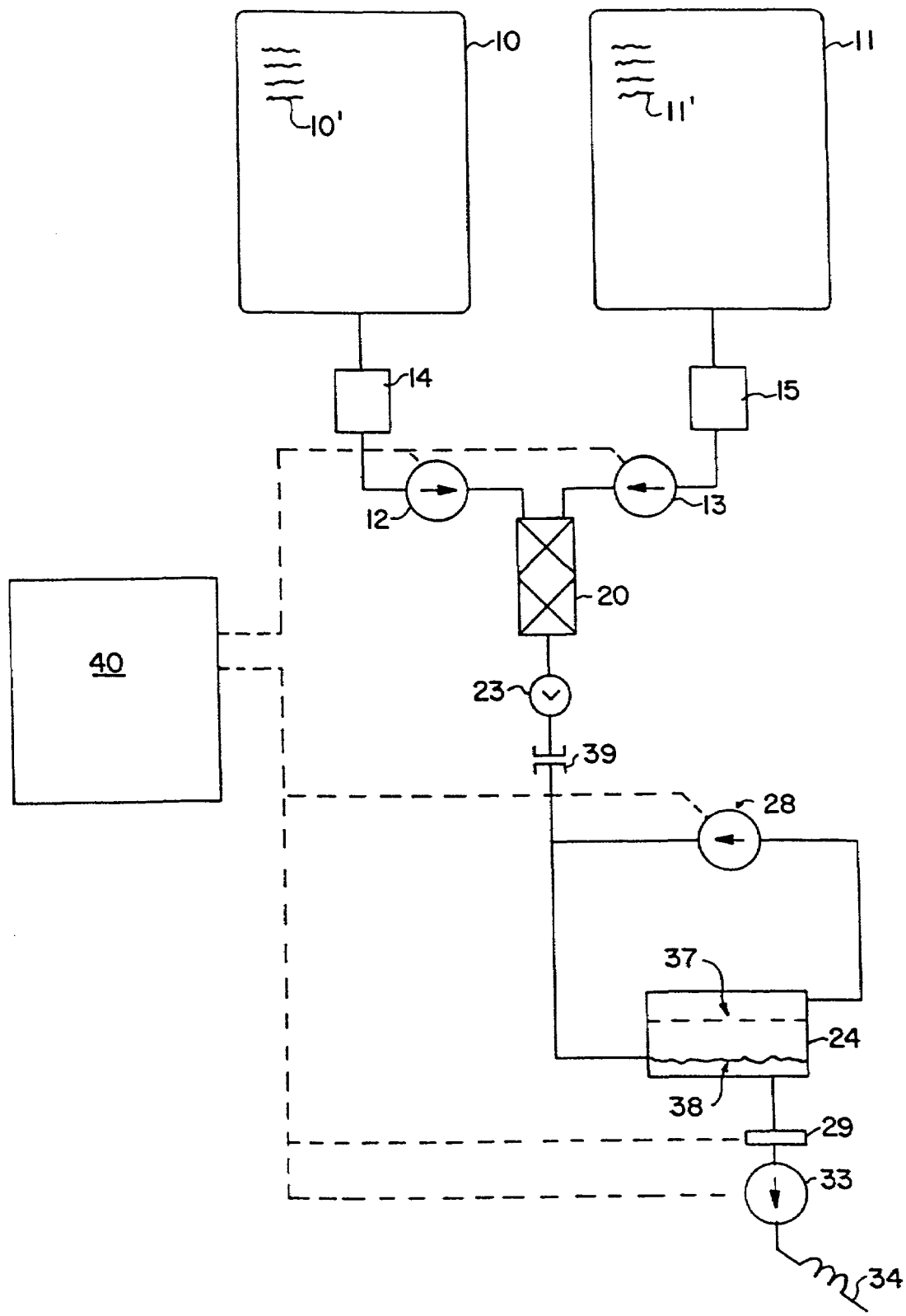
FIG. 10 is a diagrammatic showing another system for packeting flow means.

FIG. 10 shows another implementation of packetizing of the fluid flow. In this embodiment it is accomplished via air separation rather than via an intervening solid. After the fluids are mixed, they flow through a back flow valve 23. The fluid then flows through a "y" where it is mixed with packets of air. The air packets separate fluid packets, preventing back diffusion or migration of contaminants if the flow slows or stops. The wall material and diameter of the tubing is chosen so that the air packets are stable. During operation, fluid and air flow down the line to the air separating chamber 24. Here air separates itself from the fluid and moves upward through a filter 37, returning to be used again. Fluid 38 flows on to the pressurizing pump. The pulsatile air pump 28 could be a peristaltic pump, possibly operating out of phase with the fluid metering pumps so that air is injected when liquid flow is minimum from the metering pumps. After the air is separated from the liquid, the liquid flows through a fluid assurance device 29, is pressurized by the pressurizing pump 33 and flows into the patient 34. The ECS will stop the pumping if the fluid assurance detector detects any air in the line to the pressurizing pump. All of the tubing down stream from the "per patient" connector 39 is disposed of after each patient. If the flow from the metering pumps is sufficiently pulsatile, it may not be necessary to have the air pump. The momentum of flowing fluid can be sufficient to entrain packets of air between packets of fluid.

In another embodiment, see specifically FIGS. 5a and 5b, there is provided a spring loaded conical section 65 which is contained in at conical housing 66. Since this arrangement has an open fluid path when fluid is flowing, it is desireable to maintain laminar flow. This configuration has the advantage that the width of the flow path increases to accommodate increased flow. The frontal area at cross section (A), the slope of the cylinder walls and the strength of the spring can be chosen to assure that the Reynolds number stays in the laminar flow region over the designed operating range. The pressure drop and speed of flow need to be high enough that no material can diffuse against the flow. The conical surfaces need to be chosen so that they mate over a wide length. A single line of sealing is not desireable. Multiple lines of sealing are better but not the best.

It may be that redundancy is achieved by having several conical blockers in series, or conical blocker in series with a peristaltic blocker. These could be combined with sterile filters or with air gaps as set forth below. While any one can be sufficient alone, the combinations may be needed to satisfy the perceptions of the patients or hospital personnel.

Referring to FIGS. 6 and 7 of the drawings, these embodiments use similar principals but they have an air gap as the blocking means to preclude cross-contamination. Bacteria and viruses which are in a fluid cannot become airborne unless the fluid is dispersed into the air.

Present hospital practice uses drip chambers, in which fluid drips through air. They are used with most IV injections. These drip chambers are designed for flow measuring. They are part of single use disposable devices and so have no relation to cross-contamination prevention.

Figure 9:
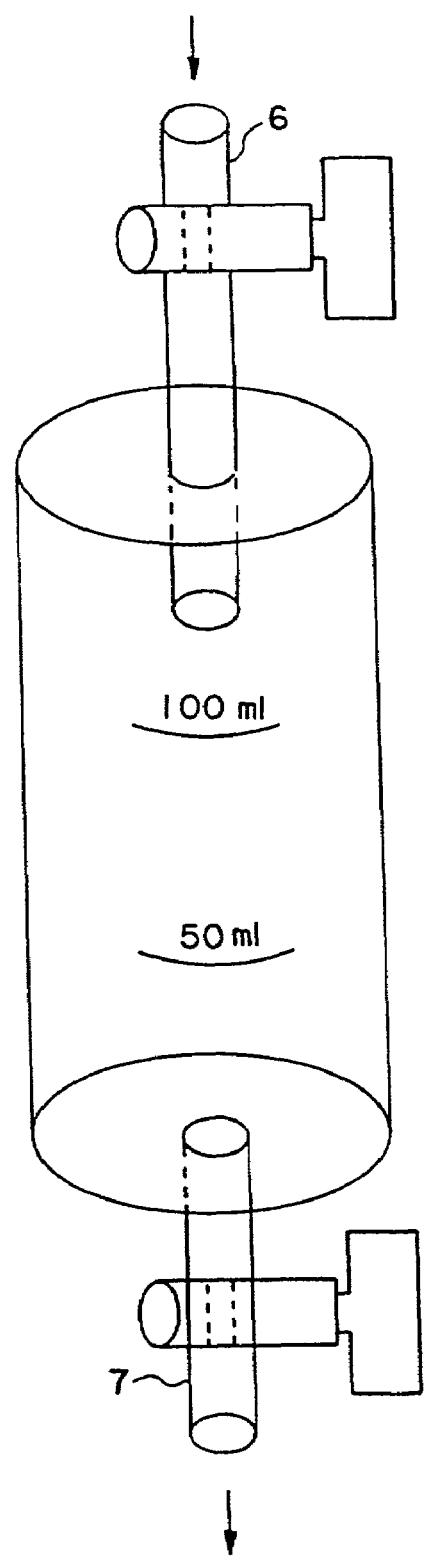
FIG. 9 is a diagrammatic showing of a disposable burette system.

Present art also included disposable burettes (FIG. 9) which can be filled from a sterile container and fluid in them then subsequently sterilely dispensed. If filled once and then dispensed into a patient, the bulk source is protected from back flow of contaminants from the patient. But if any attempt is made to have fluid flow into the burette while connected to the patient and the bulk source, they do not provide a cross-contamination barrier. This is because fluid flowing into the burette falls some distance and can cause a splash which has a possibility of carrying fluid from the bottom of the burette to the inlet nozzle. When fluid is being let out, low flow rates allow back migration of bacteria or back diffusion of virus or pyrogens. Subsequent splashing can bring these contaminants to the inlet and contaminate the remainder of the fluid path. Thus, in the embodiments below, great care is taken to eliminate potential splashing which can carry fluid across the air gap.

FIG. 6 shows a closed, sealed funnel 70 into which the fluid is tangentially injected near the top. The fluid flows around and down to the exit 71. The funnel is made of a hydrophobic plastic or has a hydrophobic coating so no string of fluid remains after flow is stopped. The area of the inflow tube and the flow rate are the variables which control the velocity of the fluid when it enters the funnel. These are chosen so a single stream, with a decreasing velocity as it flows toward the outlet, adheres to the wall of the funnel under the various flow rates for the specific application. This will eliminate splashing when the fluid stream meets the fluid pool in the bottom of the funnel. Fluid assurance devices 22 and pressurizing pump 25, etc., similar to equipment shown in FIG. 2, are found downstream from funnel 70.

In operation, the fluid injector is armed. When the start button is depressed, the metering pumps (not shown) start immediately. Mixed fluid flows into the top of the cone and collects at the bottom. This continues until several milliliters has collected in the cone and funnel geometry. The exact amount depends upon the programmed flow rate. The size of the cone needs to be sufficient to contain at least one second's worth of fluid at the programmed flow rate. After pre-filling the cone, the pressurizing pump is started. It pulls fluid from the cone and injects it into the patient. For low pressure applications, the pressurizing pump could be a peristaltic pump. For higher pressures, it preferably is a gear pump, although other types would do. Because the fluid contacting part is disposable, the gear head would be plastic, probably polycarbonate, and would mate to the durable equipment and be turned by it.

If there is air in the funnel, then there needs to be a fluid assurance device 22 at the outlet tube of the funnel, so that if something fails and the funnel is not filled, the ECS to can stop the pressurizing pump 25, preventing air from being pulled from the funnel and being delivered to the patient. There could also be a second fluid assurance after the pressurizing pump for redundance. This would be especially useful for intra-arterial injections where air injection has much more serious consequence than during IV injections.

A second embodiment for the class of blocking means forming a break in the fluid stream uses a collapsible bag 75, as shown in FIG. 7, or other large container instead of the funnel. Operation is a little different. When the arm sequence is initiated, a significant fraction of the fluid requested for the injection is pumped into the collapsible bag. This fraction could be operator controlled and depend upon the confidence the operator had that the full amount of fluid will be used. When the operator depresses the start switch, the injection starts. The metering pumps continue filling the bag at a slower rate than the pressurizing pump is withdrawing it, with the fill rate chosen so that filling is completed a few seconds before the injection is completed. The benefit of this over the funnel is the ability to start the injection and change flow rates instantaneously. The bag may be less costly than the funnel although neither part sees high pressures. A final benefit may be user perception. They may have more confidence in a device which fills an intermediate bag than in a system where there are just a few milliliters of fluid in a funnel, even though electronics and mechanics make them equally reliable.

As with the funnel, the bag needs to be made from hydrophobic material such as polypropylene so that no continuous stream of fluid remains after flow is stopped. The flow entering the bag needs to be slowed by choice of inlet diameter and tangential path so that it adheres to the wall and no splashing occurs.

While not ideal, it is possible to eliminate the static mixer by filling the bag, providing ultrasonic agitation and then pumping the mixture out. This is not as desirable because concentration cannot be changed during delivery.

By properly sizing the funnel or the bag, the need for a back flow preventer is eliminated. If the total volume of the fluid path down stream from the funnel or bag is less than the volume required to fill the funnel or bag, then back flow can never breach the air gap. If the funnel or bag volume is less than the down stream fluid path volume, then a back flow valve is needed.

It is also important that the funnel or bag be held in the proper upright position during use, since gravity is being used to assure that air surround the inlet port.

What is claimed is:

1. A method of delivering fluid to multiple patients, comprising:
   (a) providing a fluid delivery system comprising a reusable fluid path and a plurality of per-patient disposable fluid paths, the reusable fluid path including
      (i) a first fluid source;
      (ii) a second fluid source;
      (iii) a helical vane mixer adapted to mix fluids from the first and second fluid sources, the plurality of per-patient disposable fluid paths each including a first end connectable to a patient of the multiple patients and a second end connectable to the reusable fluid path;
   (b) connecting the second end of a first per-patient disposable fluid path of the plurality of per-patient disposable fluid paths to the reusable fluid path and the first end of the first per-patient disposable fluid path to a first patient of the multiple patients to define a fluid path between the first and second fluid sources and the first patient;
   (c) mixing the fluids from the first and second fluid sources to create a first mixture with a predetermined content for the first patient;
   (d) delivering the first mixture to the first patient through the first per-patient disposable fluid path;
   (e) disconnecting the first per-patient disposable fluid path from the reusable fluid path and the first patient;
   (f) connecting a second per-patient disposable fluid path to the reusable fluid path and a second patient of the multiple patients;
   (g) mixing the fluids from the first and second fluid sources to create a second mixture with a predetermined content for the second patient; and
   (h) delivering the second mixture to the second patient through the second per-patient disposable fluid path.

2. The method of claim 1, wherein the reusable fluid path further comprises at least one metering device disposed between the first and the second fluid sources.

3. The method of claim 2, further comprising a control device in communication with the metering device.

4. The method of claim 3, further comprising a user interface connected to the control device.

5. The method of claim 3, further comprising an electronic interface connecting the control device to a hospital information system.

6. The method of claim 2, wherein the at least one metering device comprises a peristaltic pump.

7. The method of claim 1, wherein the reusable fluid path further comprises a fluid assurance device.

8. The method of claim 1, wherein the first fluid source comprises a contrast source.

9. The method of claim 1, wherein the second fluid source comprises a diluent source.

10. The method of claim 1, wherein the delivery of at least one of either the first or second mixture comprises the use of a rotary valve switch to select the delivery of fluids to a patient of the multiple patients.

11. The method of claim 1, wherein the reusable fluid path further comprises a pressurizing pump.

12. A method of delivering fluid to multiple patients, comprising:
   (a) providing a fluid delivery system comprising a reusable fluid path and a plurality of per-patient disposable fluid paths, the reusable fluid path including
      (i) a first fluid source;
      (ii) a second fluid source; and
      (iii) a static mixer configured to mix the fluids from the first and second fluid sources to create a mixed fluid, the plurality of per-patient disposable fluid paths each including a first end connectable to a patient of the multiple patients and a second end connectable to the reusable fluid path;
   (b) connecting the second end of a first per-patient disposable fluid path of the plurality of per-patient disposable fluid paths to the reusable fluid path and the first end of the first per-patient disposable fluid path to a first patient of the multiple patients to define a fluid path between the first and second fluid sources and the first patient;
   (c) mixing the fluids from the first and second fluid sources to create a first mixture with a predetermined content for the first patient;
   (d) delivering the first mixture to the first patient through the first per-patient disposable fluid path;
   (e) disconnecting the first per-patient disposable fluid path from the reusable fluid path and the first patient;
   (f) connecting a second per-patient disposable fluid path to the reusable fluid path and a second patient of the multiple patients;
   (g) mixing the fluids from the first and second fluid sources to create a second mixture with a predetermined content for the second patient; and
   (h) delivering the second mixture to the second patient through the second per-patient disposable fluid path.

13. The method of claim 12, wherein the reusable fluid path further comprises at least one metering device.

14. The method of claim 13, further comprising a control device in communication with the metering device.

15. The method of claim 14, further comprising a user interface connected to the control device.

16. The method of claim 13, wherein the at least one metering device comprises a peristaltic pump.

17. The method of claim 12, wherein the reusable fluid path further comprises a fluid assurance device.

18. The method of claim 12, wherein the first fluid source comprises a contrast source.

19. The method of claim 12, wherein the second fluid source comprises a diluent source.

20. The method of claim 12, wherein the reusable fluid path further comprises a pressurizing pump.

* * * * *

UNITED STATES PATENT AND TRADEMARK OFFICE
CERTIFICATE OF CORRECTION

| | | |
|---|---|---|
| PATENT NO. | : 7,427,281 B2 | Page 1 of 1 |
| APPLICATION NO. | : 09/939656 | |
| DATED | : September 23, 2008 | |
| INVENTOR(S) | : Uber, III et al. | |

It is certified that error appears in the above-identified patent and that said Letters Patent is hereby corrected as shown below:

ON THE TITLE PAGE,

ITEM (56), under "U.S. PATENT DOCUMENTS", in Column 1, Line 66, below "4,936,832 A   6/1990   Vaillancourt" insert
-- 4,937,194A  *  6/1990  Pattillo et al. .............. 141/10 --, therefor.

IN THE SPECIFICATION

Column 1, Line 5, delete "May." and insert -- May --, therefor.

Column 1, Line 19, delete "multi-patent" and insert -- multi-patient --, therefor.

Column 5, Line 15, delete "ore" and insert -- more --, therefor.

Signed and Sealed this

Sixteenth Day of December, 2008

JON W. DUDAS
*Director of the United States Patent and Trademark Office*